(12) United States Patent
Ott

(10) Patent No.: US 8,382,983 B2
(45) Date of Patent: Feb. 26, 2013

(54) SYSTEMS AND METHODS FOR CONVERTING GASEOUS BYPRODUCTS OF WASTEWATER TREATMENT INTO ENERGY

(76) Inventor: Christopher Ott, Napa, CA (US)

( * ) Notice: Subject to any disclaimer, the term of this patent is extended or adjusted under 35 U.S.C. 154(b) by 427 days.

(21) Appl. No.: 12/577,129

(22) Filed: Oct. 9, 2009

(65) Prior Publication Data

US 2011/0084020 A1    Apr. 14, 2011

(51) Int. Cl.
*C02F 3/30* (2006.01)
(52) U.S. Cl. .......... 210/603; 210/614; 95/149; 95/187
(58) Field of Classification Search .......... 210/603, 210/615, 620, 614; 95/149, 187; 435/166; 48/127.3
See application file for complete search history.

(56) References Cited

U.S. PATENT DOCUMENTS

| | | | |
|---|---|---|---|
| 3,973,043 A * | 8/1976 | Lynn ........................ | 426/55 |
| 4,057,401 A | 11/1977 | Boblitz | |
| 4,267,038 A | 5/1981 | Thompson | |
| 6,192,833 B1 | 2/2001 | Brune et al. | |
| 6,635,177 B2 | 10/2003 | Oswald | |
| 6,656,249 B1 * | 12/2003 | Buisman et al. ............ | 95/195 |
| 6,692,642 B2 | 2/2004 | Josse et al. | |
| 6,921,485 B2 | 7/2005 | Kilian et al. | |
| 7,329,351 B2 | 2/2008 | Roberts et al. | |
| 8,017,366 B1 * | 9/2011 | Schuh et al. ............... | 435/161 |
| 2002/0079266 A1 | 6/2002 | Ainsworth et al. | |
| 2003/0111410 A1 | 6/2003 | Branson | |
| 2004/0172878 A1 | 9/2004 | Krylowicz | |
| 2004/0182779 A1 | 9/2004 | Dilian et al. | |
| 2006/0138047 A1 | 6/2006 | Morgoun | |
| 2006/0213370 A1 * | 9/2006 | Leonard et al. ............. | 96/243 |
| 2006/0272502 A1 * | 12/2006 | Van Grinsven et al. ...... | 95/235 |
| 2007/0114182 A1 | 5/2007 | DePoli | |

FOREIGN PATENT DOCUMENTS

| | | |
|---|---|---|
| JP | 2007-297605 | 11/2007 |
| WO | 2008/092604 | 8/2008 |

OTHER PUBLICATIONS

Ott, Christopher, International Search Report, PCT/US09/50567, Dated Oct. 23, 2009.
Ott, Christopher, Written Opinion, PCT/US09/50567, Dated Oct. 23, 2009.
Ott, Christopher, U.S. Appl. No. 12/173,751, filed Jul. 15, 2008, Non-final Office action dated May 28, 2010.
Ott, Christopher, U.S. Appl. No. 12/173,751, filed Jul. 15, 2008, Non-final Office action dated Jan. 20, 2011.
Ott, Christopher, U.S. Appl. No. 12/173,751, filed Jul. 15, 2008, Notice of Allowance Office action dated Sep. 19, 2011.
Ott, Christopher, Application No. PCT/US2010/051022 Int'l Filing Date Sep. 30, 2010, International Search Report dated Feb. 7, 2011.
Ott, Christopher, Application No. PCT/US2010/051022 Int'l Filing Date Sep. 30, 2010, Written Opinion dated Feb. 7, 2011.

* cited by examiner

*Primary Examiner* — Fred Prince
(74) *Attorney, Agent, or Firm* — EcoTech Law Group, P.C.

(57) ABSTRACT

A method for removing methane from biogas is described. The method includes: (i) receiving biogas including methane and other components into a first tank; (ii) receiving water into the first tank; (iii) contacting the biogas with the water inside the first tank; (iv) dispensing methane gas from an outlet of the first tank; and (v) producing from the tank an effluent stream that includes other components of the biogas.

25 Claims, 7 Drawing Sheets

SYSTEMS AND METHODS FOR CONVERTING GASEOUS BYPRODUCTS OF WASTEWATER TREATMENT INTO ENERGY

BACKGROUND OF THE INVENTION

The present invention relates generally to wastewater treatment. More particularly, the present invention relates to novel treatment systems and methods which use treated water and byproducts (e.g., biogas and various gases) of a wastewater treatment process to generate energy.

Conventional wastewater treatment begins with pretreatment of wastewater, which is carried out in different stages. In an initial stage, wastewater undergoes hydrolysis to convert particulate matter to soluble compounds. These soluble compounds are degraded in a next stage. By way of example, fermentation degrades sugars and fatty acids present in wastewater to produce acetate, hydrogen, and oxygen. Ultimately the degraded compounds are converted to methane gas by anaerobic digestion, typically using methanogenic organisms. Anaerobic digestion is a simple process that can greatly reduce the amount of organic matter which might otherwise be destined to be land filled or be burnt in an incinerator. Almost any organic material can be processed with anaerobic digestion, including biodegradable waste materials such as waste paper, grass clippings, leftover food, sewage, and animal waste.

After pretreatment concludes, certain conventional methods may rely on passive techniques, which rely upon nothing more than gravity, to remove suspended solids from wastewater. Typically, a primary sedimentation vault, large enough to store 30 million gallons of water, is employed to carry out sedimentation. Sedimentation is a slow process where relatively heavy solids in wastewater are allowed to settle, such that they sink to the bottom of the vault and produce a discrete solid phase containing heavy solids and a discrete liquid or water phase. As a result, these type solids easily separate from the liquid phase of wastewater.

After heavy solids are removed, wastewater is transported into another large tank to remove organic matter. In this large tank, microorganisms adhere to the thick walls and bottom layer of the tank and thrive under appropriate light, temperature, and surface area in the tank. These microorganisms grow in large enough numbers and consume most of the oxygen and food (i.e., organic matter) present in wastewater. In the absence of conditions necessary to sustain, microorganisms eventually die, leaving behind wastewater that is enriched with nitrogen and phosphorous. Conventional methods discharge this wastewater to the soil, ponds, or tanks, depending on the amount of other remaining contaminants.

Unfortunately, conventional wastewater treatment suffers from several drawbacks. For example, not only is the reliance on sedimentation for removal of solids a long and drawn out process, but is also very expensive. Specifically, infrastructure, such as a large tank, pipes, and pumps, represent significant capital costs.

As another example, the process of removing organic matter, like the process of solid removal, is also passive and expensive as it is carried out over long periods of time in a large tank. As yet another example, conventional treatment methods do not offer provisions for effective removal of dead microorganisms and residual nitrogen and phosphorous from wastewater. Although processes like reverse osmosis or ion exchange are known to remove nitrogen and phosphorous, they are not deemed commercially viable and are therefore not integrated into conventional wastewater treatment methods.

In addition to passive treatments, the conventional wastewater systems introduce into the atmosphere noxious gases, such as methane, $CO_2$, $SO_X$, and $NO_X$, as byproducts that are believed to contribute to the greenhouse effect.

What is therefore needed are systems and methods of wastewater treatment that more effectively and rapidly treat wastewater and account for the release of noxious gases into the atmosphere.

SUMMARY OF THE INVENTION

In view of the foregoing, this invention provides novel systems and methods for wastewater treatment that more effectively and rapidly treat wastewater using anaerobic digestion as an initial step.

Conventional wastewater treatments typically release noxious gases into the environment, contributing to the greenhouse effect. The present invention provides novel systems and methods for capturing those gases, converting those gases into useful energy, and doing so preferably in a substantially closed system. It is an objective, among many, of the present invention to convert otherwise harmful byproducts to useful energy, preferably using some of the treated water resulting from wastewater treatment.

The approach adopted by the present invention recognizes, among other things, that the concept of biochemical oxygen demand ("BOD") drives various steps of wastewater treatment. BOD is a well known parameter which indicates the amount of oxygen needed to biologically stabilize the organic matter present. According to preferred embodiments of the present invention, efforts to effectively control BOD levels in various stages of wastewater treatment rely upon more than gravity and time. This allows the present invention to offer active treatment of wastewater, as opposed to prior art's passive treatment, which relies only upon gravity and time.

Organic matter commonly present in wastewater uses oxygen for various reasons and as a result, depletes soluble oxygen. A requisite high level of dissolved oxygen, however, is desirable during certain stages of treatment to grow microorganisms to consume organic matter present in wastewater treatment. Conventional methods only in a single discrete step grow microorganisms by introducing oxygen to replenish the depleted levels of oxygen in wastewater. This step provides oxygen to initially promote growth of naturally occurring microorganisms to large numbers so that they consume almost all of the organic matter and oxygen in wastewater. Conventional methods introduce oxygen by implementing passive means, i.e., requiring a large space-consuming tank to expose a greater surface area to the atmosphere for long periods of time.

The present invention recognizes the need to maximize use of high-pressure air diffusion in multiple steps to actively increase the amount of dissolved oxygen in wastewater as well as creating an active environment for naturally occurring and custom introduced bacteria to grow by increasing the surface-area-to-volume ratio in specific reactors. In preferred embodiments of the present invention, this process of actively introducing oxygen and increasing surface-area-to-volume ratio begins early, during a solids-removal stage, and well before microorganisms growth is encouraged in conventional methods.

When sufficient amount of microorganisms die in an oxygen- and nutrient-poor environment, dead organisms undergo decay, raising levels of ammonia, nitrate, and nitrite through a process known as "nitrification." Conventional treatment discharges the wastewater with a high concentration of nitrogen and phosphorous to the environment. Reverse osmosis and ion exchange are known to remove nitrogen and phosphorous, but are not deemed commercially viable and are therefore not integrated into conventional wastewater treatment methods.

Discharge of nutrient-rich effluent is known to be injurious to life. Nitrates are carcinogenic and direct discharge of wastewater with nitrates can contaminate drinking water aquifers. The present invention recognizes this and prevents such contamination by effectively removing nitrogen and phosphorous from wastewater before discharge.

Preferred embodiments of the present invention effectively treat wastewater by driving down BOD, maintaining the level of dissolved oxygen, lowering the solid content, and controlling the nutrient level in wastewater at various stages. By way of example, in one stage, the present invention drives down BOD and solid content in wastewater by actively focusing on the removal of BOD-contributing solids.

As another example, during the process of removing solids, the present invention also focuses on improving the growth regime for naturally occurring and genetically engineered bacteria. Preferred embodiments of the present invention use high-pressure air diffusion to substantially maintain or increase the level of dissolved oxygen in wastewater. As a result, according to preferred embodiments of the present invention, microorganism growth is encouraged well before they are employed to remove organic matter.

As yet another example, directly after removal of organic matter by microorganism consumption, preferred embodiments treat wastewater by creating anaerobic conditions to achieve complete microorganism die off and lower solid content or reduce BOD in wastewater. Next, the wastewater is treated to remove solids and further reduce BOD in an aerobic environment which replenishes the dissolved oxygen levels.

As yet another example, preferred embodiments of the present invention, while actively removing BOD-contributing solids, dead microorganisms, nutrients, algae, and other solids, maintain the level of dissolved oxygen in wastewater to prevent an increase of BOD and solid content by reversible reaction. It is important to note that prior art fails to recognize drawbacks of reversible reactions which increase BOD, let alone offer provisions to prevent increase of BOD.

As yet another example, preferred embodiments of the present invention drive down the nutrients in wastewater by actively focusing on the removal of all forms of nitrogen and phosphates by effectively cultivating specific biological processes that utilize nutrients available for their own growth. The invention further reduces the nutrient load by actively removing any biological matter remaining in the effluent.

As yet another example, the present invention offers provisions to capture methane and other components of biogas to convert methane into electricity and to convert other components of biogas and byproducts of the electricity conversion process to chemical species which promote growth or production of useful products. In preferred embodiments of the present invention, a portion of treated water resulting from wastewater treatment is used in conjunction with biogas and gases produced during anaerobic and aerobic digestion, respectively, in a useful manner as opposed to releasing such gases to the atmosphere, as conventional processes do.

In one aspect, the present invention provides a method for removing methane from biogas. The method includes: (i) receiving biogas including methane and other components into a first tank; (ii) receiving water into the first tank; (iii) contacting the biogas with the water inside the first tank; (iv) dispensing methane gas from an outlet of the first tank; and (v) producing from the tank an effluent stream that includes other components of the biogas. The step of contacting may include passing bubbles of biogas through the water. Water may be obtained from any source of purified water. Preferably, however, water is obtained from a wastewater treatment facility.

In one embodiment of the present invention, the inventive methods may further include a step of carrying out digestion of water enriched with organic matter in a second tank to produce the biogas. The second tank may be different from the first tank. The organic matter in the water may be between about 0.5% by volume and about 25% by volume.

In preferred embodiments of the present invention, inventive methods include a step of sending the effluent stream from the tank to a diffused air flotation ("DAF") tank that is designed to effect removal of solids.

Inventive methods may further include a step of sending the methane gas to an electrical generator that is designed to burn methane gas and produce electrical energy. Preferably, the electrical generator produces exhaust gases which include at least one of $CO_2$ gas, $SO_x$ gas, and $NO_x$ gas, and are treated in a third tank by contacting the exhaust gases with water to remove at least one of $CO_2$ gas, $SO_x$ gas, and $NO_x$ gas from the third tank and produce water having dissolved therein at least one of $CO_2$ gas, $SO_x$ gas, and $NO_x$ gas. More preferably, the water having dissolved therein at least one of $CO_2$ gas, $SO_x$ gas, and $NO_x$ gas is delivered to an algal pond. The algal pond may be a high rate algal pond ("HRAP").

In another aspect, the present invention provides a method for removing byproduct gases after aerobic digestion. The method includes: (i) receiving into a first tank a gaseous mixture including at least one of ammonia gas and sulfur gas; (ii) receiving water into the first tank; (iii) contacting the gaseous mixture including at least one of the ammonia gas and the sulfur gas with the water inside the first tank to produce an effluent stream of water having dissolved therein the at least one of aqueous ammonia and sulfur and produce a residual gaseous mixture including at least one of ammonia gas and sulfur gas; (iv) dispensing residual gas including at least one of residual ammonia gas and residual sulfur gas; and (v) discharging the effluent stream including water which has dissolved therein the at least one of aqueous ammonia and sulfur gas. Residual gaseous mixture refers to the gas or gases that do not dissolve in water. The step of dispensing may include recirculating the residual gaseous mixture from outlet of the first tank to an inlet of the first tank. The step of contacting may include passing bubbles of the gaseous mixture through the water.

In preferred embodiments of the present invention, the inventive method may further include carrying out in a second tank aerobic digestion of wastewater that produces the gaseous mixture including at least one of the ammonia gas and the sulfur gas. Preferably, the content of organic matter in the wastewater after aerobic digestion is between about 0% by volume and about 4% by volume. Water may be purified water obtained from any source. Preferably, however, purified water is obtained from a wastewater treatment plant. Aerobic digestion may be carried out in a biological chip reactor ("BCR").

Preferred embodiments of the present invention may further include the steps of: (i) detecting concentration of aqueous ammonia by percent in the effluent stream; and (ii) conveying an effluent stream including water which has dissolved therein at least one of aqueous ammonia and sulfur to a tank which either breaks down aqueous ammonia or consumes sulfur, if amount of aqueous ammonia in the effluent water stream is greater than or equal to a predetermined value, or conveying the effluent stream to an algal pond if amount of aqueous ammonia in the effluent stream is less than the predetermined value. In preferred embodiments of the present invention, the predetermined value is between about 0 ppm and about 10 ppm, depending primarily on the concentration of ammonia in a feed stream that is being reduced by oxidation, e.g., in the BCR reactor. Preferably, the algal pond is an HRAP.

In yet another aspect, the present invention provides a system for removing byproducts of anaerobic digestion. The system includes: (i) a first tank including: (a) a first inlet that is connected to receive byproduct gases of anaerobic digestion including at least one gas and methane, (b) a first outlet that provides methane gas as exhaust, (c) a second inlet that is connected to receive a stream of water, and (d) a second outlet that discharges an effluent water stream having dissolved therein the above-mentioned at least one gas into a tank designed for removing solids; and (ii) an electrical generator that is connected to the first outlet of the first tank; and wherein the first tank is designed to contact the stream of water with the byproduct gases of anaerobic digestion and produce the effluent stream of water. In preferred embodiments, the electrical generator produces electricity and a gas including at least one of $CO_2$ gas, $SO_x$ gas, and $NO_x$ gas.

In preferred embodiments, the present invention further provides a second tank that includes: (i) a first inlet that is connected to receive the gas including at least one of $CO_2$ gas, $SO_x$ gas, and $NO_x$ gas produced in the electrical generator; (ii) a first outlet that is designed to dispense a residual gas including at least one of $CO_2$ gas, $SO_x$ gas, and $NO_x$ gas; (iii) a second inlet that is configured to receive a stream of water; (iv) a second outlet that is designed for discharging water which has dissolved therein at least one of $CO_2$ gas, $SO_x$ gas, and $NO_x$ gas; and (v) wherein the second tank is configured to contact the stream of water with the gas to produce the effluent water having dissolved therein at least one of $CO_2$ gas, $SO_x$ gas, and $NO_x$ gas and produce residual gas including at least one of residual $CO_2$ gas, residual $SO_x$ gas, and residual $NO_x$ gas. Preferably, the second outlet of the second tank is connected to an algal pond. The present invention further provides a system wherein the first outlet is communicatively coupled to the first inlet such that the residual gas including at least one of $CO_2$ gas, residual $SO_x$ gas, and residual $NO_x$ gas is recycled or provided back to the second tank.

In yet another aspect, the present invention provides a system for wastewater treatment. The system includes: (i) a solids-removal subassembly designed to remove solids from wastewater and produce solids-depleted water; (ii) an assembly designed for processing organic material in the solids-depleted wastewater to produce treated water and the assembly connected to the solids-removal subassembly; (iii) a tank that has a first inlet, a first outlet, and a second outlet; and (iv) wherein the first inlet of the tank is designed to receive treated water, the first outlet is designed to discharge a first portion of treated water, the second outlet is designed to discharge a second portion of treated water, and the first portion of treated water is used for processing byproduct gases resulting from wastewater treatment. Preferably, the tank may be a holding tank that is located downstream from a nutrient-removal tank which is designed to remove nutrients from wastewater. In alternative embodiments of the present invention, the tank is a nutrient-removal tank designed to remove nutrients from wastewater In preferred embodiments, present invention includes a solids-removal subassembly that includes at least one of: (i) a solids separator; (ii) a DAF tank which includes: (a) a pored diffuser; and (b) a high-pressure water pump fitted with a venturi tube for drawing in air, for forming air bubbles, and for forcing the air bubbles through the pore diffuser to form micro-air bubbles in wastewater; and (iii) a first sedimentation removal tank ("SRT") designed to remove solids from wastewater using diffused air flow which maintains dissolved oxygen in wastewater at a substantially constant level. The present invention further provides for the assembly designed for processing organic material in the solids-depleted wastewater to include at least one of one or more BCRs and an aerobic sludge digester.

In preferred embodiments, the present invention further includes an anaerobic tank to carry out anaerobic digestion wherein a first amount of the first portion of treated water is used to process the byproduct gases including methane and at least one gas resulting from anaerobic digestion. The system preferably also includes a first tank which is designed to contact the byproduct gases including methane gas and the at least one other gas with the first amount of the first portion of treated water to produce methane exhaust and effluent water including the at least one other gas. In certain embodiments of the present invention, the first amount of the first portion of treated water refers to the entire amount of the first portion of treated water.

In other preferred embodiments, the present invention further includes: (i) an electrical generator; and (ii) a first connection which is designed to connect to the first tank the electrical generator such that methane exhaust from the first tank is conveyed to the electrical generator to produce electricity and produce a gas including at least one of $CO_2$ gas, $SO_x$ gas, and $NO_x$ gas. In the above-mentioned embodiments, the system further includes a second tank which is designed to contact a second amount of the first portion of treated water with the gas including at least one of $CO_2$ gas, $SO_x$ gas, and $NO_x$ gas to produce water having dissolved therein at least one of $CO_2$ gas, $SO_x$ gas, and $NO_x$ gas, and produce a residual gas including at least one of residual $CO_2$ gas, residual $SO_x$ gas, and residual $NO_x$ gas. It is not necessary that a second amount of the first portion of treated water with the gas. Rather, preferred embodiments of the present invention may use a new stream of water, or the entire amount of treated water to contact the gas. Any pure stream of water can be used to contact the gas so that soluble components inside the gas will dissolve in water. In the interest of water conservation, however, it is preferable that a certain amount of the first portion of water be used. Regardless of which stream of water and how much of it is used to contact the gas, the present invention preferably includes an algal pond which is designed to receive water having dissolved therein at least one of $CO_2$ gas, $SO_x$ gas, and $NO_x$ gas.

In yet another embodiment, the present invention may further include a third tank which is designed to contact a first portion of water with said byproduct gases including at least one of ammonia gas and sulfur gas that is generated during aerobic digestion of wastewater.

In another aspect, the present invention provides a method of wastewater treatment. The method includes the steps of: (i) removing solids from wastewater to produce solids-depleted water; (ii) processing organic material in the solids-depleted wastewater to produce treated water; (iii) discharging a first portion of treated water and a second portion of treated water; and (iv) using the first portion of treated water to process byproduct gases resulting from wastewater treatment. In preferred embodiments, the present invention provides the further step of removing nutrients from wastewater. The above-mentioned step of using may be carried out after removing nutrients.

In preferred embodiments, the inventive methods further include the steps of: (i) conducting anaerobic digestion in an anaerobic digestion tank to produce the byproduct gases including methane and at least one gas; and (ii) contacting in a first tank a first amount of the first portion of treated water with the byproduct gases to produce methane exhaust and treated water including the at least one gas. Preferably, the invention further includes the step of conveying methane to an electrical generator and producing electricity and gases including at least one of $CO_2$ gas, $SO_x$ gas, and $NO_x$ gas. The inventive method may further include the step of contacting in a second tank a second amount of the first portion of treated water with the gases to produce treated water having dissolved therein at least one of $CO_2$ gas, $SO_x$ gas, and $NO_x$ gas, and a residual gas including at least one of residual $CO_2$ gas, residual $SO_x$ gas, and residual $NO_x$ gas. The inventive method may yet further include the steps of: (i) sending the treated water having dissolved therein at least one of $CO_2$ gas, $SO_x$ gas, and $NO_x$ gas to an algal pond; and (ii) recirculating back to the second tank the residual gas including at least one of residual $CO_2$ gas, residual $SO_x$ gas, and residual $NO_x$ gas.

In preferred embodiments, the present invention further includes the steps of: (i) conducting aerobic digestion in a BCR (in the presence of biological chips) and producing the byproduct gases including at least one of ammonia gas and sulfur gas; and (ii) contacting in a tank a first portion of the treated water with the byproduct gases including at least one of ammonia gas and sulfur gas to produce treated water having dissolved therein at least one of aqueous ammonia and sulfur and produce a residual gas including at least one of residual ammonia gas and residual sulfur gas. Preferably, the present invention includes the further steps of: (i) conveying to an algal pond the treated water including at least one of aqueous ammonia and sulfur if the amount of aqueous ammonia in the treated water is less than a predetermined value, or (ii) conveying to the BCR the treated water including at least one of aqueous ammonia and sulfur if the amount of ammonia in the treated water is greater than or equal to the predetermined value. In a preferred embodiment of the present invention, the predetermined value is between about 0 ppm and about 10 ppm, depending primarily on the concentration of ammonia in a feed stream that is being reduced by oxidation, e.g., in the BCR reactor.

The construction and method of operation of the invention, however, together with additional objects and advantages thereof will be best understood from the following descriptions of specific embodiments when read in connection with the accompanying figures.

DETAILED DESCRIPTION OF THE PREFERRED EMBODIMENTS

In the following description numerous specific details are set forth in order to provide a thorough understanding of the present invention. It will be apparent, however, to one skilled in the art that the present invention may be practiced without limitation to some or all of these specific details. In other instances, well known process steps have not been described in detail in order to not unnecessarily obscure the invention.

Figure 1A:
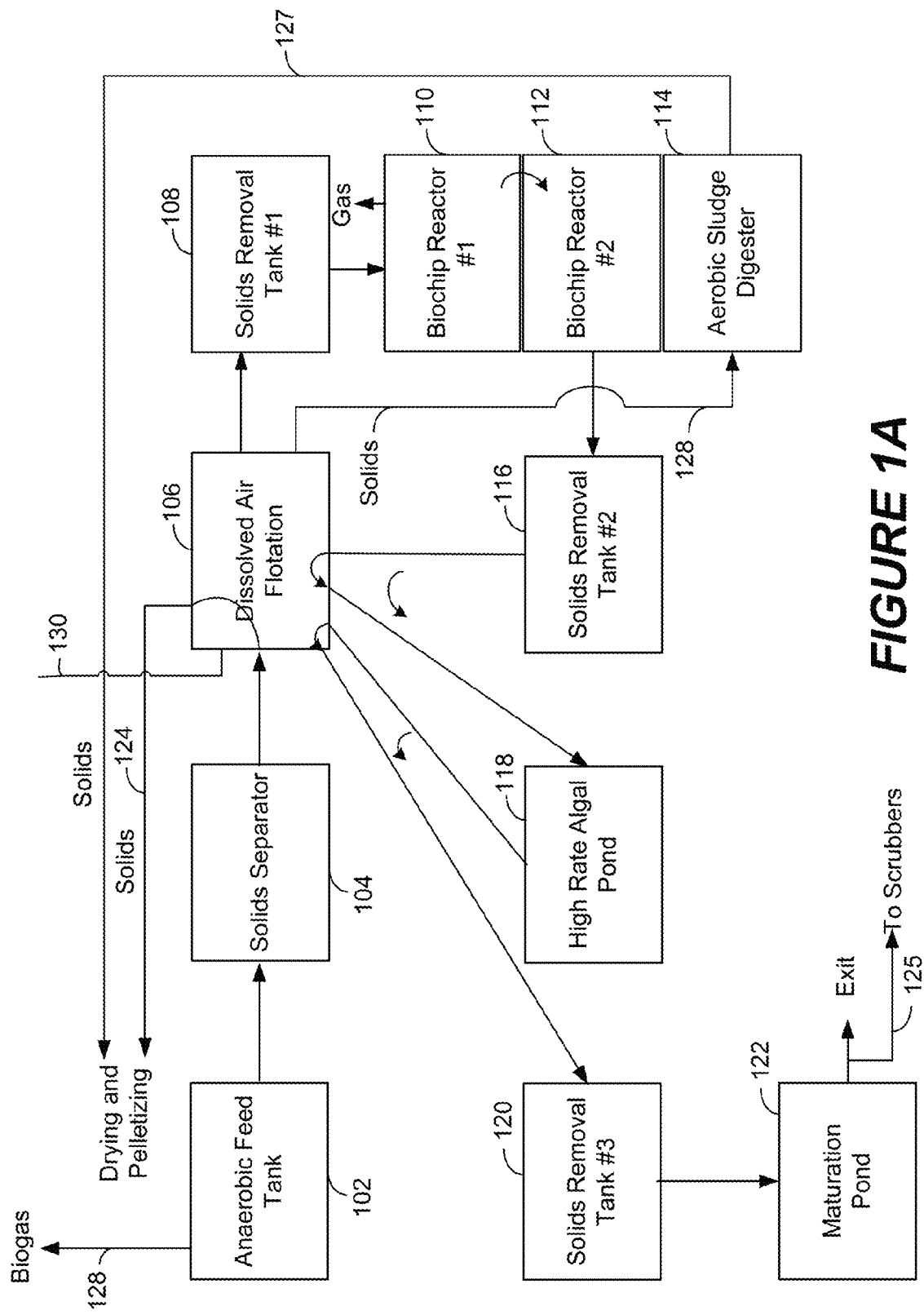
FIG. 1A shows a system for wastewater treatment, according to one embodiment of the present invention.

FIG. 1A shows a system design 100, according to one embodiment of the present invention, for active treatment of wastewater. System 100 includes an anaerobic tank 102, inside which anaerobic digestion of wastewater takes place. In other words, inside anaerobic tank 102, organic content in wastewater is broken down into simpler molecules which can be further treated by other methods. A byproduct of anaerobic digestion, biogas 128, is collected at the top surface of anaerobic tank 102 (not shown to simplify illustration) and delivered to a system for treatment resulting in product that can be converted into clean energy (described below with reference to FIGS. 1B and 5).

System design 100 provides wastewater that has undergone anaerobic digestion to a series of active devices for removal of solid waste. These active devices include a solids separator 104, a DAF tank 106, and a first SRT 108, each of which facilitates removal of solid contaminants of different sizes and type. The relatively solid-free wastewater is then transported to a series of BCRs 110 and 112 to remove organic matter. For removal of solid sludge, if necessary, an aerobic sludge digester tank 114 is provided. Wastewater containing dead microorganisms from either BCR 112 or from aerobic sludge digester 114, if one is employed, is sent to a second SRT 116 for removal of solids which include for the most part dead microorganisms. For further removal of dead organisms, the wastewater is treated in DAF tank 106 and from there sent to HRAP 118. HRAP 118 is provided to remove nutrients, such as nitrates, nitrites, and phosphorous from the wastewater. Next, wastewater is passed again through DAF tank 106 and through a third SRT 120 to specifically remove algae introduced into wastewater from HRAP 118. DAF tank 106 also serves to increase level of dissolved oxygen in wastewater. The nutrient-and-algae-depleted wastewater is optionally provided to a maturation pond 122 before discharging to the environment. In maturation pond 122, residual algae not removed in either DAF tank 106 or SRT 120 is removed and treated wastewater is exposed to elements of the natural environment. In preferred embodiments of the present invention, a portion of the effluent stream flowing through line 125 from maturation pond 122 facilitates conversion of various byproducts of wastewater treatment (described below with reference to FIGS. 1B and 1C) to useful energy (described below with reference to FIG. 5) or useful downstream products (described below with reference to FIGS. 1B, 1C, and 5).

System 100 also includes various lines or connections between the different tanks to transport residual solids that are removed from the wastewater. According to FIG. 1A, one such line 124 is provided between DAF tank 106 and anaerobic tank 102 to transport those solids which are not removed after treatment in DAF tank 106 back to a subsystem for drying and pelletizing. Another line 127 is also provided to transport solids, which typically include dead microorganisms, from aerobic sludge digester 114 to a subsystem designed for drying and pelletizing. The resulting pellets are used for fertilizer. According to the embodiment shown in FIG. 1A, residual solids are not only transported from aerobic sludge digester 114, but are also transported to digester 114. Specifically, a line 128 is provided to transport residual solids from DAF tank 106 back to aerobic sludge digester 114.

In addition to conveying wastewater at different stages of treatment and conveying residual solids, various lines or connections between the different tanks of system 100 deliver biogas and gas to produce energy and other useful downstream products. By way of example, a gaseous mixture 128 which includes methane and other gases captured as byproducts of anaerobic digestion inside anaerobic tank 102 is transported to a tank 126 shown in FIG. 1B. In preferred embodiments of the present invention, tank 126 is a scrubber designed to contact gaseous mixture 128 with liquid stream 125. As another example, a portion of effluent stream 125 from maturation pond 122 is used to contact gaseous mixture 142 of FIG. 1C. FIG. 1C, described in greater detail below, shows processing of the gas or gaseous mixture resulting from aerobic digestion.

Figure 1B:
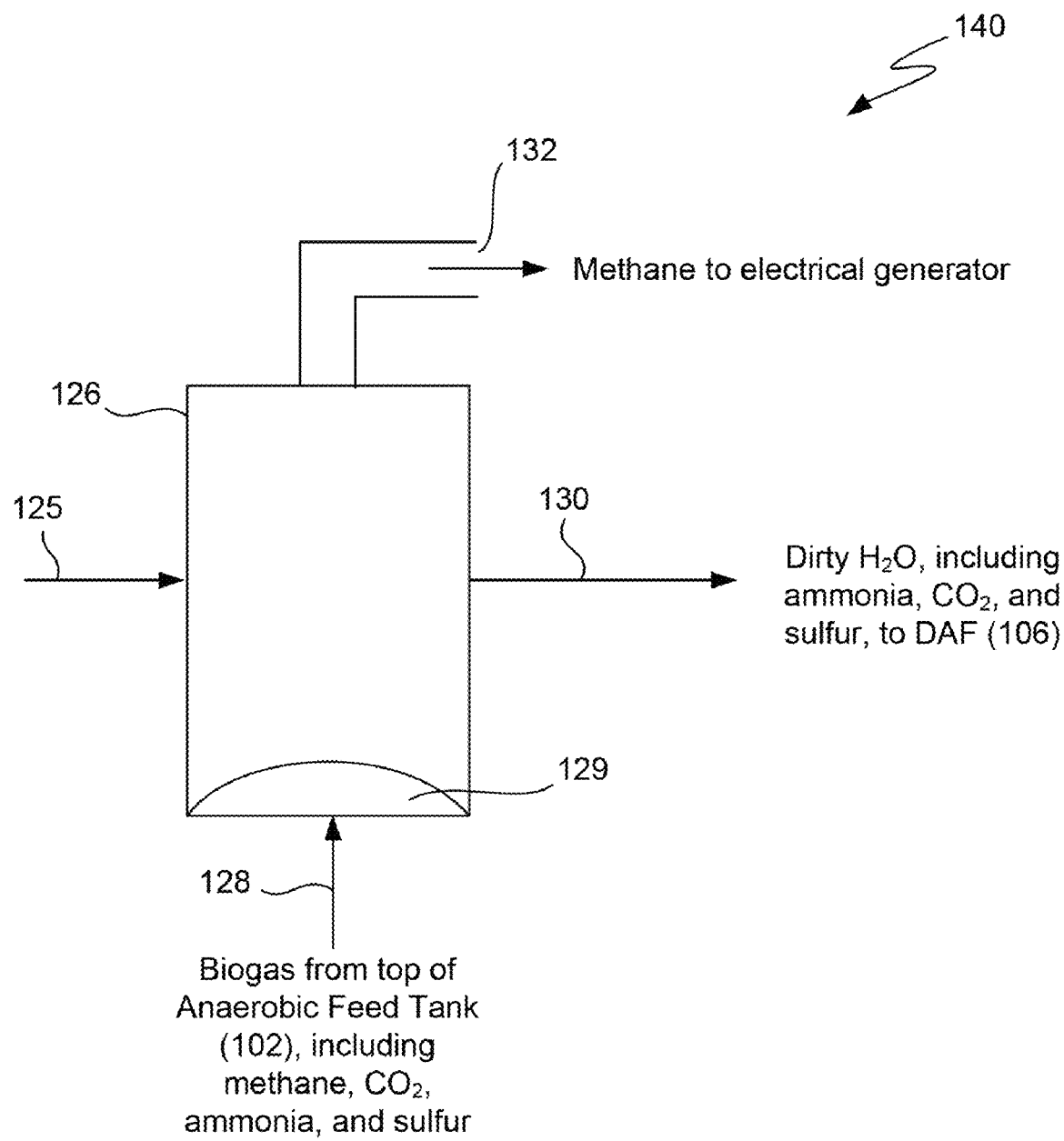
FIG. 1B shows a system, according to one embodiment of the present invention, for separating methane gas from biogas that is produced after anaerobic digestion.
Figure 1C:
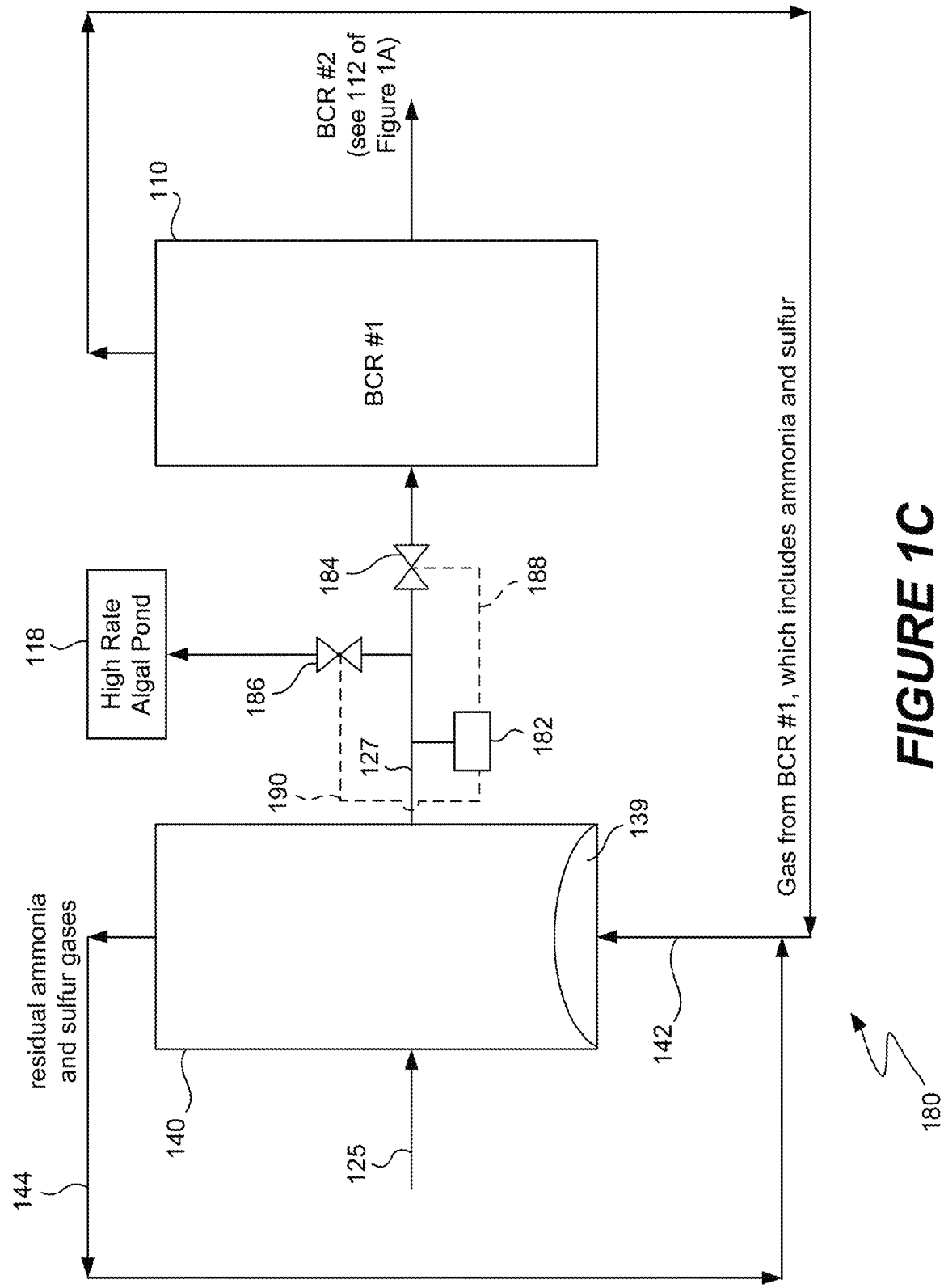
FIG. 1C shows a system, according to one embodiment of the present invention, for treating gas produced by aerobic and anaerobic digestion.

From tank 126 of FIG. 1B, a line 130 is provided to DAF tank 106 (as shown in FIG. 1A) to deliver an effluent water stream having dissolved therein certain biogas components, such as ammonia, carbon dioxide, hydrogen, and sulfur, but not including methane, for further treatment. A detailed description of FIG. 1B explains how the effluent entering DAF tank 106 shown in FIG. 1A is produced.

In system 100, gas (which includes ammonia gas and sulfur gas) emanating from processing of organic matter inside BCR 110 (shown in FIG. 1A) is delivered via line 142 to a tank 140. Tank 140 is preferably a scrubber that is configured to contact a portion of treated water 125 (shown in FIGS. 1A and 1B), for example, with the gas generated inside BCR 110. In other embodiments of the present invention, instead of using a portion of treated water stream 125, any water stream that is relatively pure can be used.

Solids separator 104 comes equipped with a screen designed to remove solids that do not settle out in anaerobic tank 102 or that are pulled into system 100 by the inlet pumps (not shown to simplify illustration of FIG. 1A). Solids in wastewater that pass through the screen are pressed between at least two belts, each of which is supported by turning rollers positioned throughout the press. The belts are permeable and allow wastewater to pass through, holding back heavy solids. Moving action of the belt and the splashing of wastewater, as it permeates the belt, also serve to introduce oxygen into wastewater. The resulting increased level of dissolved oxygen encourages growth of microorganisms, which remove organic matter in a subsequent step.

Depending on the screen size, solids separator 104 removes between about 75% and about 98% of solids removed from wastewater, which at this stage of treatment typically has a solid content that is between about 15% and about 30%. Eliminating these solids represents a significant amount of BOD removal. Solids removed by the press may be composted or otherwise removed from the premises for disposal. solids separator 104 can be made from any rigid material, but is preferably made from stainless steel. Similarly, a range of suitable dimensions work well. In one preferred embodiment of the present invention, system 100 uses a solids separator commercially available from Press Technologies of Wheat Ridge, Colo.

DAF tank 106 captures small particulate matter that is not removed by solids separator 104. To effect solid separation from wastewater, DAF tank 106, in accordance with one embodiment of the claimed invention, uses a pored diffuser and a high-pressure pump that is preferably fitted with a venturi tube and is designed to introduce air bubbles inside wastewater. The pump draws in air, forcing air bubbles through the pored diffuser to form micro-air bubbles. The pored diffuser may be made from stone. Air is forced through the pored diffuser to produce a diffused air flow, preferably of about 40 cubic feet per minute. Air bubbles in their upward motion accumulate on the particulate matter and carry with them particulate matter to the top, where they are removed via skimmers.

Air bubbles inside DAF tank provide a large surface area to effectively dissolve oxygen and thereby raise the level of soluble oxygen in wastewater. As a result, air bubbles not only facilitate removal of solids, but also increase the level of dissolved oxygen in wastewater to promote microorganism growth for subsequent removal of organic matter. Thus, the present invention promotes conditions for effective removal of organic matter in early stages and well before such removal is the primary focus during subsequent treatment.

In preferred embodiments of the present invention, DAF tank is commercially available from Martint Environmental of Lexington, S.C. By way of example, a DAF tank used in the present invention is about 7 feet long, 3.5 feet wide, and 5 feet high. Hydraulic residence time in a DAF tank may be between about 1 and about 3 hours. Hydraulic residence time refers to the amount of time it takes for a single molecule of water to pass through the unit from the time it enters a tank, for example, to the time it leaves. DAF tank removes between about 85% and about 95% of the solids removed from wastewater, which at this point has a solid content that is between about 3% and about 6%.

Unlike conventional solid sedimentation in the prior art, the present invention does not require solids to fully settle to the bottom of the SRT to be trapped there. SRT 108 effects separation of residual solids by actively increasing the hydraulic flow path and providing physical impediments to particles for permanently trapping them. Hydraulic flow path refers to a path that is traversed by wastewater. An increase in the hydraulic flow path allows for separating a greater amount of solids from wastewater.

SRT 108 is preferably large enough such that it takes wastewater being pumped in at 40 gallons per minute 100 minutes to fill it. U.S. Pat. No. 6,899,808, which is incorporated herein by reference for all purposes, describes preferred embodiments of the SRT used in the present invention. Surface area inside SRT 108 is preferably between about 160 square feet and about 320 square feet. SRT removes between about 85% and about 90% of solids having particle sizes greater than 20 micrometers from wastewater, which at this point has a solid content of about 1%. During the solid removal process, SRT 108 effects diffused air flow to raise level of dissolved oxygen in wastewater and to clean the screens provided for solid removal. By reducing BOD level and solid content and raising level of dissolved oxygen in wastewater, the present invention promotes conditions for removal of organic matter in early stages and well before such removal is the primary focus during subsequent treatment.

Figure 2:
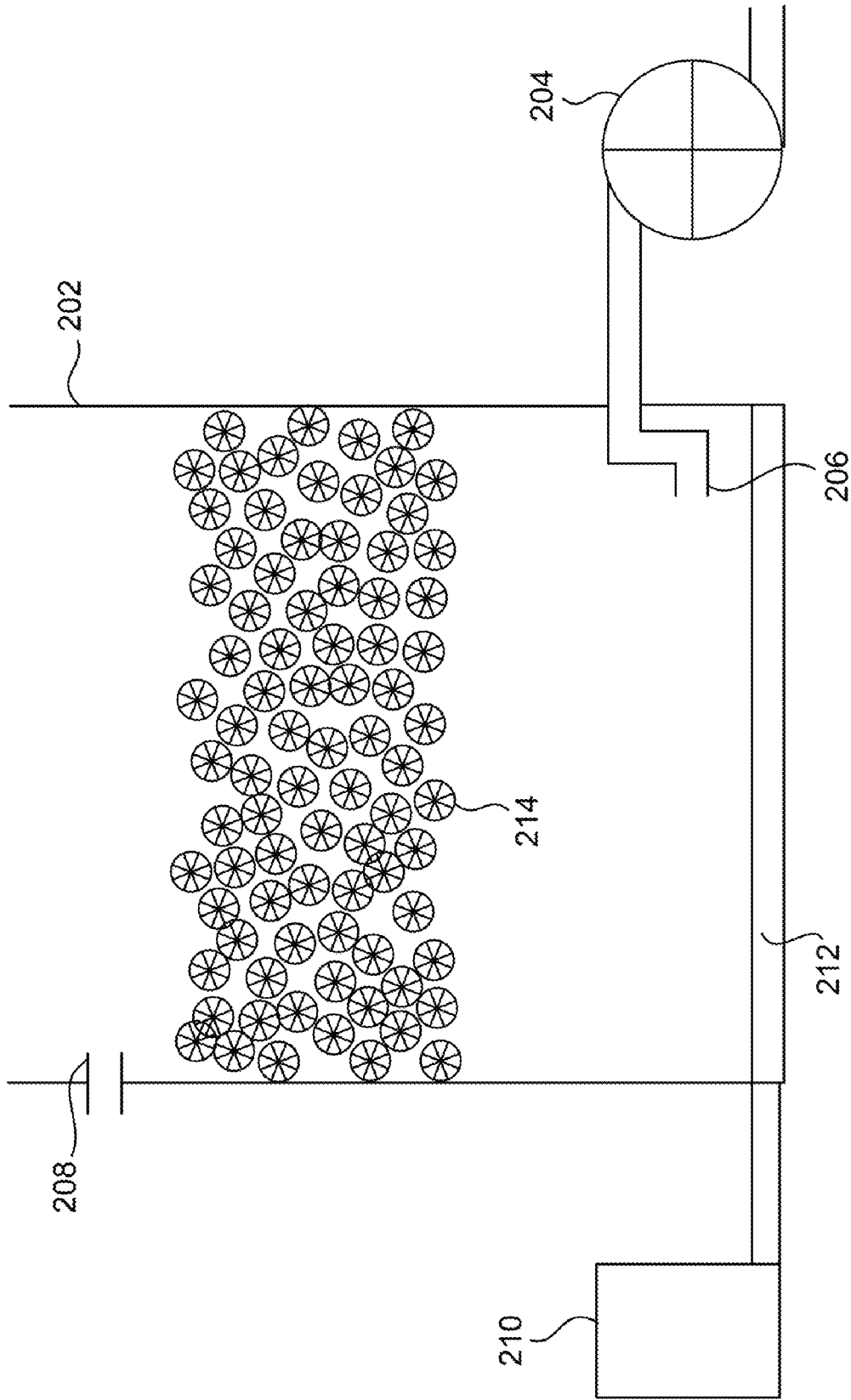
FIG. 2 shows details of a BCR design, according to one embodiment of the present invention, used in the system of FIG. 1A.

FIG. 2 shows a cross-sectional view of a BCR 200 (e.g., BCRS 110 and 112), in accordance with one embodiment of the present invention. BCR 200 includes a tank 202, which contains biological chips 214 and has an inlet 208 for providing wastewater (not shown to simplify illustration) for treatment. Tank 202 is equipped with a blower 204 which introduces air inside wastewater. Waste solids in wastewater form a layer 212 and are removed by a pump 210. Biological chips 214 and blower 204 serve to provide wastewater with very high dissolved oxygen concentration and a high surface-area-to-volume ratio to aid the metabolic growth rates of microorganisms (not shown in FIG. 2 to simplify illustration).

BCR is an aerobic treatment system that utilizes microorganisms attached to biologic chips to form a biological film or slime layer (typically ranging from 0.1 mm to 0.2 mm thick). Microorganisms in the outer part of slime layer degrade the organic material in wastewater. However, as the slime layer thickens, oxygen is unable to penetrate the biological chips and anaerobic organisms develop. Eventually the microorganisms near the surface lose their ability to cling to the biological chips, and a portion of the slime layer falls off.

In accordance with one embodiment of the present invention, microorganisms inside a BCR include aerobic, anaerobic and facultative bacteria, fungi, and protozoa. BCR 110 is preferably designed to contain many different types of microorganisms, each of which is ideally suited to remove at least one type of organic matter from wastewater. By way of example, BCR 110 uses heterotrophic bacteria (e.g., *Achromobacter, Alcaligenes, Arthrobacter, Cirtomonas, Flavobacterium, Pseudomonas,* and *Zoogloea*) for removal of BOD. BOD is created by any matter containing a carbon molecule normally present in wastewater and that is generated from any one of human waste, food waste, animal waste, and plant waste.

Blower 204 is effective in providing oxygen to microorganisms in wastewater. Size of bubbles formed in wastewater from pumping air and the amount of air pumped dictate the amount of oxygen dissolved in wastewater. Those skilled in the art will recognize that small bubbles can be twice as efficient at transferring oxygen because they provide greater surface area of air per mass of air. Bubbles also mix wastewater inside the BCR to ensure that nutrients in wastewater are in constant contact with the bacteria that consumes them.

The presence of biological chips provides a high surface area inside the reactor to which the microorganisms may affix. By way of example, the ratio of surface area inside the BCR to volume of BCR is between about 32 square feet per cubic foot and about 130 square feet per cubic foot. Preferably, however, the ratio of surface area inside the BCR to volume of BCR is about 73.5 square feet per cubic feet. High surface area combined with high oxygen concentration aide the metabolic rates of microorganisms. The affixed microorganisms quickly remove all available food in the form of organic particulate matter (which contribute to BOD) from the reactor and leave a situation of high metabolic rates and low amounts of food (i.e., there is a low ratio of food to microorganism). Over a period of time, most solids in the reactors continue to be active and remove more BOD from the influent water. Eventually, as more and more of the food is depleted inside the reactor, the microorganisms die from starvation.

BCR 112 is preferably designed to contain at least one type of microorganism which removes at least one type of organic matter that is particularly difficult to remove from the wastewater in BCR 110 or requires additional processing time, i.e., above and beyond the processing time in BCR 110. According to the present invention, it is also possible to have additional BCRs, in addition to BCRs 110 and 112, to facilitate effective organic matter removal. By way of example, an initial step of nitrification is carried out in BCR 112 by autotropic bacteria Nitrosomonas, which converts ammonia to nitrite, despite the fact that some nitrifying bacteria exists in BCR 110. A third BCR (not shown in FIG. 1A to simplify illustration) may be used for a subsequent step of nitrification using autotropic bacteria Nitrobacter.

In preferred embodiments of the present invention, BCRs 110 and 112 are about 7 feet long, 10.5 feet wide, and 8 inches in height. Temperature inside BCRs is preferably between about 15° C. and about 33° C., and the hydraulic residence time is preferably about 8 hours. According to one embodiment of the present invention, BCRs are about 40% filled with small biorings, have 133 cubic feet per minute of diffused air flowing through it during operation, and use 6 ounces of defoaming agent per day. In cold climates, where heat dissipation is relatively high, it is preferable to keep substrate levels high to carry out nitrification effectively. The term "high substrate levels" means keeping a certain level of biological matter (sludge) inside the BCR to maintain its thermal mass and avoid wide temperature swings inside the BCR and/or also means keeping the bacteria count high to accommodate the greater die-off rate when temperatures drop.

The present invention's use of a BCR, individually or in combination with other BCRs, represents an active process because it is provides air and constantly places bacteria in contact with nutrients through circulation of wastewater to effectively encourage nutrient uptake. Furthermore, the surface area inside the BCR is also optimized for removal of organic waste.

Aerobic sludge digester 114 is one type of BCR, except that it is designed to remove sludge. In other words, digester 114 contains microorganisms which are known to consume, and therefore remove, sludge.

Although the BCRs and aerobic sludge digesters remove organic matter and lower the BOD, they leave wastewater rich with nitrates from the endogenous decay of microorganisms that have run out of food source. To this end, previously described DAF tank 106 and a second SRT, shown as SRT 116 in FIG. 1A, are used to remove dead microorganisms. To remove dead microorganisms, DAF tank 106 is provided with another chamber, separate from the chamber which is used to remove from wastewater solids that are not dead microorganisms. HRAP 118 is used in system 100 to remove nutrients from wastewater.

Figure 3:
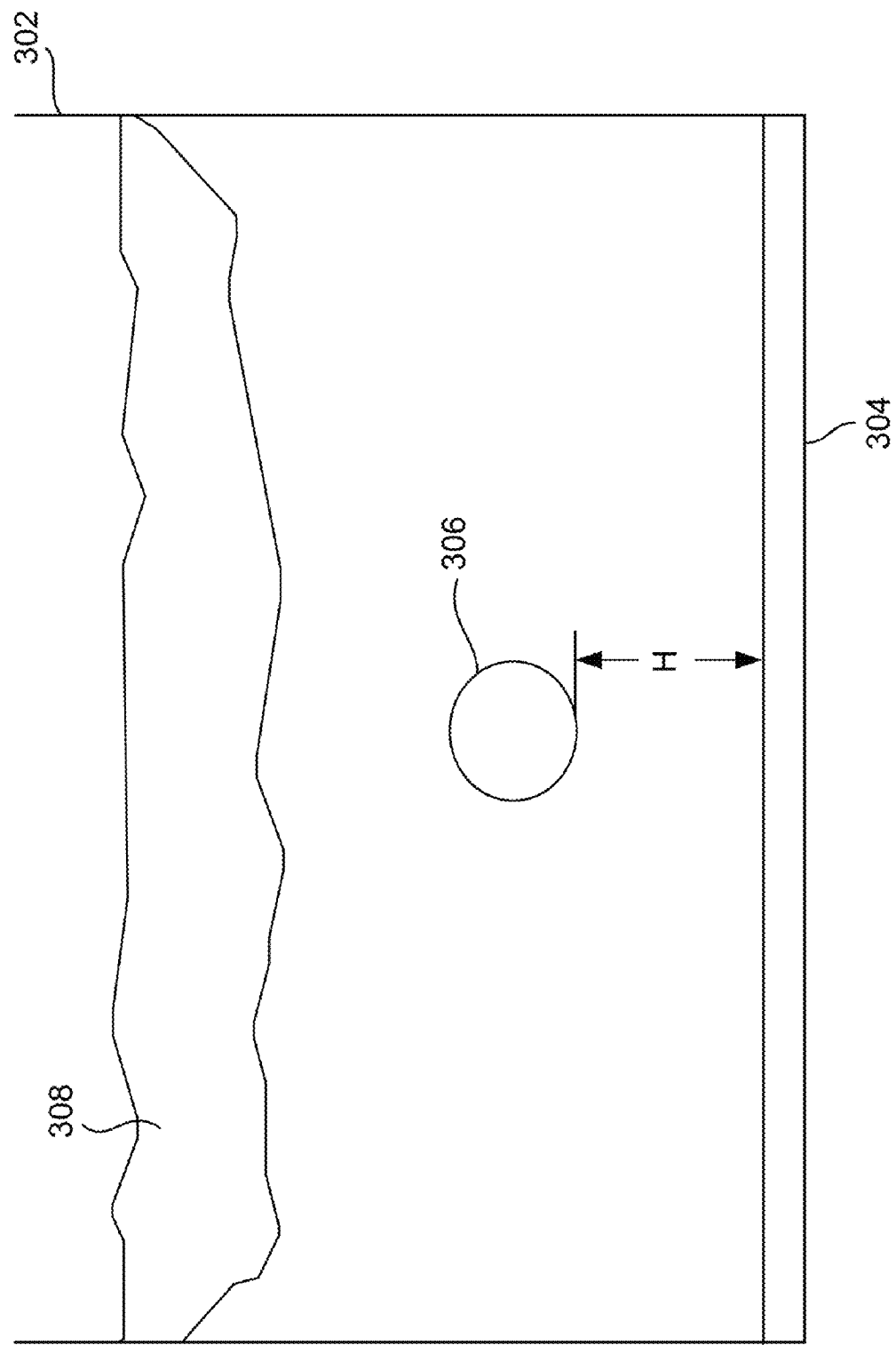
FIG. 3 shows an inventive algal pond used in the system of FIG. 1A.

FIG. 3 shows HRAP 300, according to one preferred embodiment of the present invention. HRAP 300 includes a tank 302 containing algae 308. A spectrum of radiation 306 operates at wavelengths that range from about $10^2$ nm and $10^6$ nm This spectrum of radiation is preferably disposed at a location that is between about ⅓ and about ½ the depth of HRAP 300. At the bottom of tank 302, a solid waste layer 304 accumulates which may ultimately be removed. A hydraulic pump and a paddle (both not shown to simplify illustration) are preferably provided in HRAP 300 for stirring and aeration of wastewater. Aeration and stirring facilitates driving up the dissolved oxygen level in wastewater to promote algae growth. Tank 302 is preferably maintained at a temperature that is between about 21° C. and 35° C.

Figure 4:
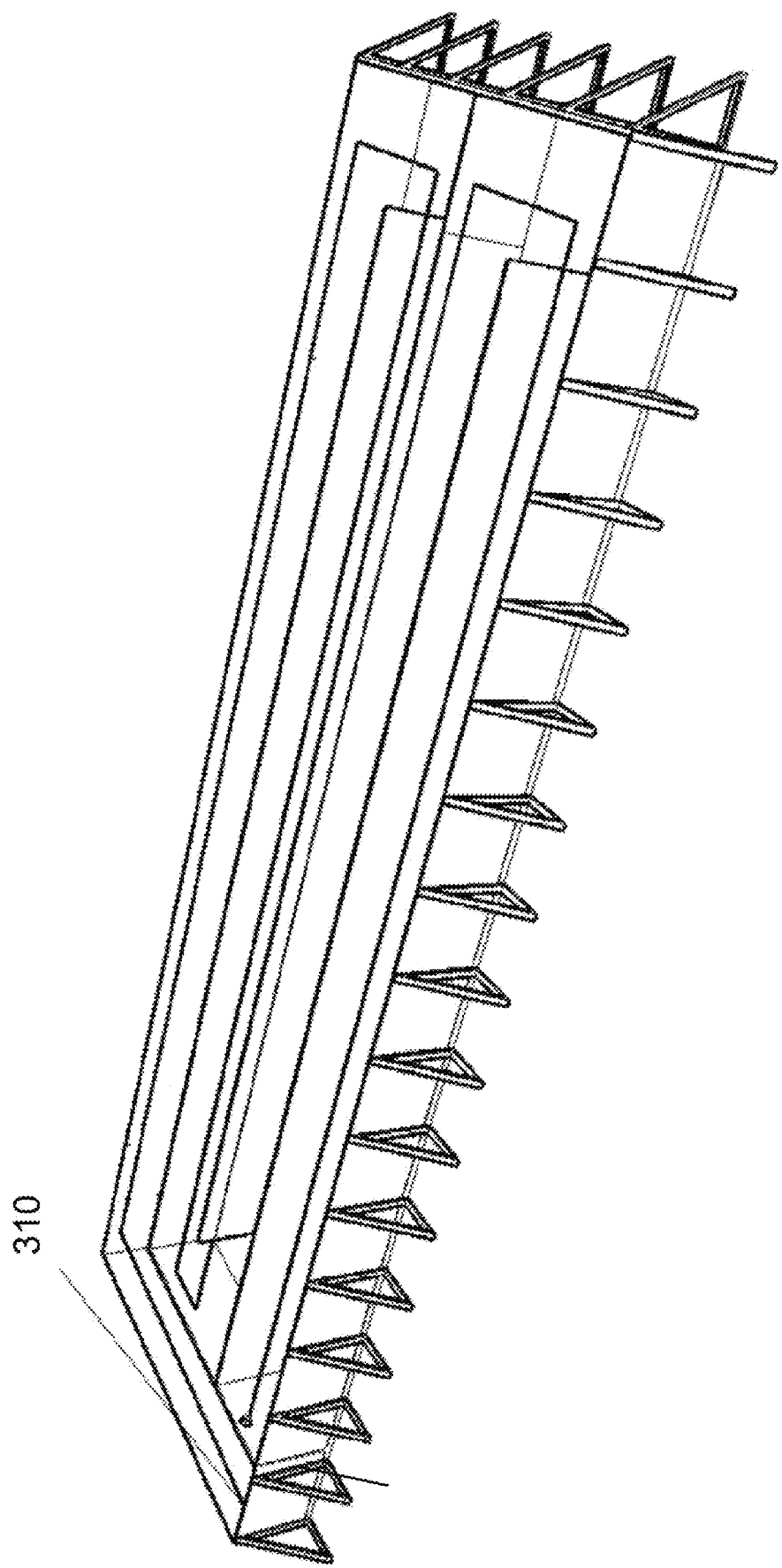
FIG. 4 shows a perspective view of the algal pond of FIG. 3.

FIG. 4 shows a perspective view of HRAP 300, in accordance with one preferred embodiment of the present invention. Inside HRAP 300 wastewater is preferably guided through a channel, which allows the water to traverse back and forth along a length of tank 302. The channel carves out a hydraulic path for wastewater and is preferably serpentine in shape.

HRAP can have any dimensions that effectively remove nutrients from wastewater. The present invention recognizes, however, that nutrient load and flow rate of wastewater drive HRAP dimensions. By way of example, HRAP has a length of about 24 feet, a width of about 77 feet, and a height of about 4 feet. HRAP preferably provides a surface area that is between about 1000 square feet and about 50,000 square feet and, more preferably, about 1848 square feet for wastewater treatment. The channel length is preferably between about 200 feet and about 3000 feet. Inside the channel of HRAP, wastewater moves at a velocity of 10 inches per second and has a residence time of about 72 hours.

HRAP primarily uses algae to remove nitrates and phosphates from wastewater. Growth rate of algae is dictated by available oxygen, temperature, light, and nutrients. Conventional algal ponds are very shallow because they facilitate introduction of oxygen and penetration of light to promote algae growth. Unfortunately, for processing relatively large volumes of wastewater, conventional algal ponds are very large, i.e., they are typically measured in hectares.

The present invention preferably uses an HRAP, which is deeper and not so spread out. In preferred embodiments of the present invention, it both aerates and stirs wastewater to effectively introduce oxygen. Furthermore, a radiation source inside the HRAP effectively facilitates penetration of light through greater depths of wastewater. As a result, HRAPs according to the present invention can occupy as little as 160 square meters for 120-cubic-meters-per-day flow systems.

Preferably contemporaneous with above-described treatment of wastewater, the present invention also treats byproducts resulting from wastewater treatment. To this end, FIG. 1B shows a system 140, according to one embodiment of the present invention, for separating methane gas from other components of biogas that are produced after anaerobic digestion in wastewater. Although this system and other such systems which process byproducts of wastewater treatment can function either in a contemporaneous or non-contemporaneous manner relative to wastewater treatment, in preferred embodiments, inventive systems and methods process the byproducts in a contemporaneous manner to increase throughput and avoid byproduct build-up.

System 140 includes a tank 126, preferably a scrubber, for removal of methane 132 so that it can subsequently be used as energy source (described below with reference to FIG. 5). Tank 126 includes a first inlet for receiving a stream of water (e.g., a portion of treated water 125 from maturation pond 122 of FIG. 1A), a first outlet for dispensing an effluent water stream 130 having dissolved therein certain components of biogas, a second inlet for receiving biogas 128 produced after anaerobic digestion, and a second outlet for methane exhaust 132. As shown in FIG. 1A, methane, one component of biogas, is a residual gas as it is not soluble in water.

Tank 126 can receive a water stream from any source of water or pure water. In the interest of water conservation, the present invention recognizes that a portion of treated wastewater resulting from wastewater treatment can be used for processing byproducts of wastewater treatment.

Tank 126 preferably comes equipped with a bubbler 129 to produce bubbles. Specifically, bubbler 129 introduces biogas 128 inside a tank full of water in the form of micro-bubbles. The bubbles provide a large surface area between the biogas/water interface to facilitate dissolving certain soluble biogas components in water. Residual methane gas exits tank 126 and is further processed as described below in system 170 of FIG. 5.

Figure 5:
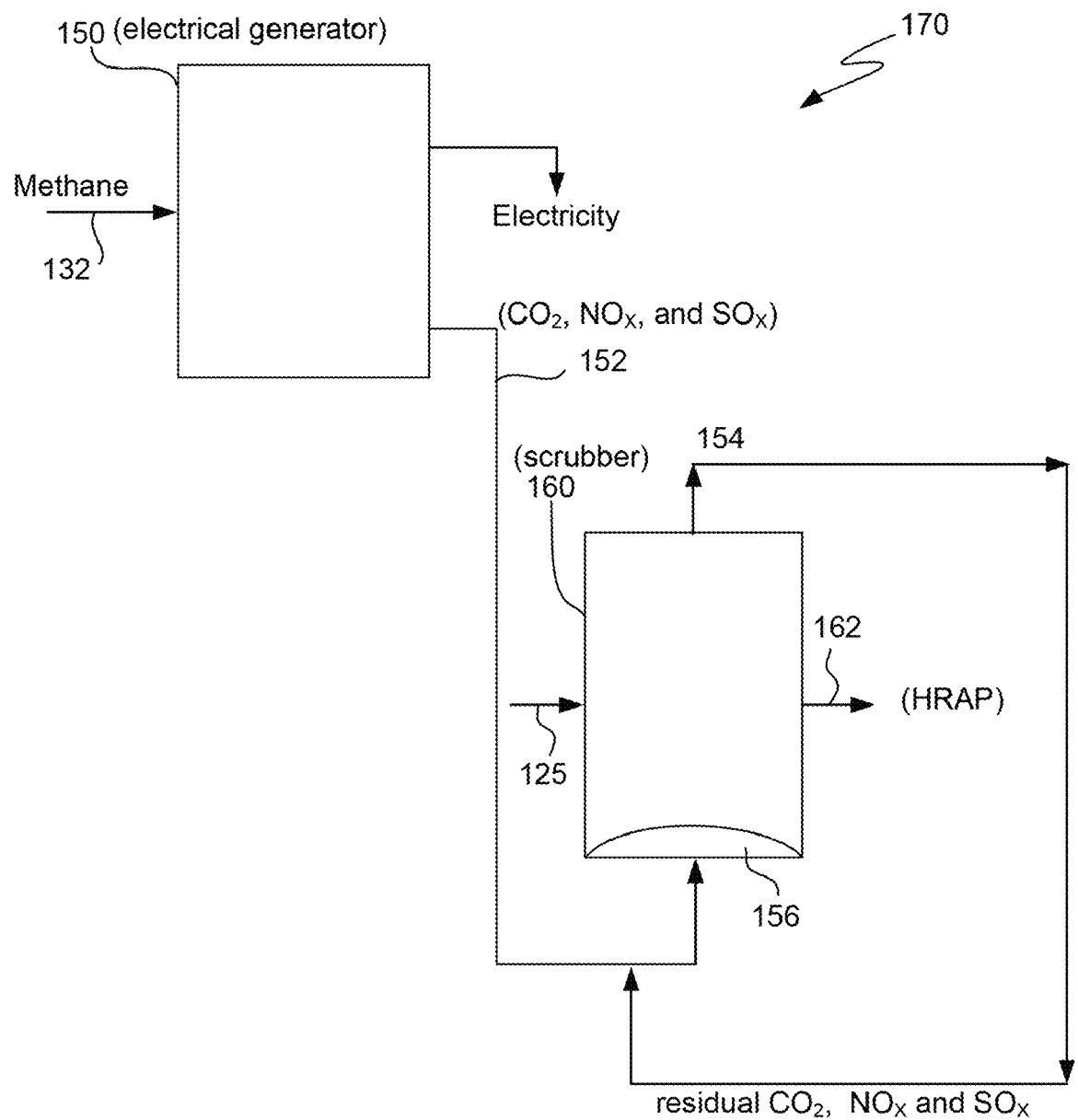
FIG. 5 shows a system, according to one embodiment of the present invention, for converting methane gas into electricity.

FIG. 5 shows a system 170, according to one embodiment of the present invention, for converting methane exhaust into electricity and for converting residual gases resulting from an electricity generator to a simpler, less complicated molecular form that can be used by HRAP 118 of FIG. 1A to foster growth of algae, which is useful for producing, among other things, biofuels. System 170 includes an electrical generator 150 and a tank 160, which is preferably a scrubber. Electrical generator 150 uses methane exhaust 132 (generated inside tank 126 of FIG. 1B) to generate electricity and a produce a gaseous mixture 152 (e.g., including at least one of $CO_2$, $SO_x$, and $NO_x$), which are fed into a tank 160. According to FIG. 5, a portion of treated water 125 from maturation pond 122 of FIG. 1A enters tank 160 such that it contacts gaseous mixture 152 of tank 160. A bubbler 156, similar to bubbler 129 of FIG. 1B, ensures that the gaseous mixture in the form of micro bubbles contacts water to facilitate dissolving components of the gaseous mixture in water. As a result, a certain amount of the gaseous components of mixture 152 dissolve in the treated water to form water 162 that is enriched with aqueous components (i.e., predominantly at least one of $CO_2$, $SO_x$, and $NO_x$). As shown in FIG. 5, this gas-enriched water stream 162 is advanced to HRAP 118 of FIG. 1A, where algae production is promoted by the dissolved gaseous components in water. The residual gases, which include remaining amounts of at least one of $CO_2$, $SO_x$, and $NO_x$ that did not dissolve in treated water are recycled back to tank 160 via line 154 for further treatment. The goal of the recycling feature of FIG. 1B is to ultimately dissolve all of $CO_2$, $SO_x$, and/or $NO_x$ gases in water and advance these gases to HRAP 118 of FIG. 1A to promote algae growth.

FIG. 1C shows a system 180, according to one embodiment of the present invention, for processing gas (i.e., predominantly ammonia gas and sulfur gas) produced by BCR 110 of FIG. 1A. According to this figure, gaseous byproducts resulting from aerobic digestion of wastewater that is carried out in BCR 110, are transported to a tank 140, preferably a scrubber, for processing. Like tank 160 of FIG. 5 and tank 126 of FIG. 1A, tank 140 of FIG. 1C comes equipped with bubbler 139, which introduces the gas produced in BCR 110 in the form of micro bubbles through the tank full of treated water to facilitate dissolving in water of those components of the gaseous byproducts that are soluble in water Tank 160 includes a first inlet for receiving water and a first outlet for dispensing water which is enriched with at least a soluble amount of gaseous components that dissolve. In preferred embodiments of the present invention, the water is treated water 125 from maturation pond 122 of FIG. 1A. However, it is possible to so treat the gaseous byproducts with a water stream obtained from any source. Tank 140 has a second inlet for receiving gas from BCR 110 and a second outlet for dispensing the residual gas that does not dissolve in water.

An ammonia concentration sensor 182 is located downstream from tank 140 and is capable of controlling the flow of effluent stream from tank 140 to either HRAP 118 or back to BCR 110. To this end, ammonia sensor 182 is communicatively coupled to two different valve assemblies 184 and 186 via control lines 188 and 190, respectively. When ammonia concentration sensor 182 detects ammonia concentration in the effluent stream of tank 140 to be either equal to or greater than a predetermined concentration value, sensor 182 activates valve assembly 184 to convey an effluent stream of tank 140 to BCR 110 for further treatment. In the alternative, when sensor 182 detects ammonia concentration in the effluent stream to be less than the predetermined concentration value, sensor 182 activates valve assembly 186 to convey the effluent stream to HRAP 118. In preferred embodiments of the present invention, the value of predetermined ammonia concentration lies in a range that is between about 0 ppm and about 10 ppm, depending primarily on the concentration of ammonia in a feed stream that is being reduced by oxidation, e.g., in the BCR reactor. An effluent stream with low ammonia concentration suggests nitrogen is present in the effluent stream in a less complex form which is useful for promoting algae growth in HRAP 118. In contrast, a high ammonia concentration suggests that the effluent stream does not have sufficient amount of nitrogen in simple form to facilitate algae growth in HRAP 118. Those skilled in the art will recognize that although system 180 is shown in connection with BCR 110, a similar system could be used to process the gas emanating in BCR 112 of FIG. 1A. Regardless of whether gas emanating from BCR 110 or BCR 112 is processed as described above, if the concentration of ammonia in the effluent stream of a scrubber, for example, is greater than or equal to a predetermined concentration value, then that effluent stream is sent back to the BCR so that the dissolved aqueous ammonia in the effluent stream can be broken down to a simpler form which is ultimately useful to promote algae growth in HRAP 118.

Similar to ammonia gas, sulfur is another gaseous byproduct of aerobic digestion carried out in BCR 110 or BCR 112 of FIG. 1A. Instead of or in addition to using an ammonia concentration sensor, system 180 of FIG. 1C may include a sensor for detecting the concentration of sulfur gas (not shown to simplify illustration) if the presence of sulfur gas is expected or suspected as a byproduct of aerobic digestion. Those skilled in the art will recognize that the valve assemblies, similar to those shown in connection with the ammonia concentration sensor, can be used in conjunction with the sulfur concentration sensor. Since sulfur naturally dissipates faster relative to ammonia, it is not necessary in preferred embodiments of the present invention to monitor the sulfur concentration in the same way as the ammonia concentration. In even more preferred embodiments of the present invention, only the ammonia concentration is measured and so long as that concentration is less than a predetermined value, it is safe to assume that the sulfur concentration is also sufficiently low to advance the effluent stream from tank 140 to HRAP 118.

In preferred embodiments of the present invention, electrical generator 150 is commercially available from General Electric, Inc.'s Jenbacher gas engine division located in Jenbach, Austria. However, other electrical generators which use methane to generate electricity will work also.

In preferred embodiments of the present invention, tank 126 (in system 140 of FIG. 1B), tank 140 (in system 180 of FIG. 1C), and tank 160 (system 170 of FIG. 5) are large enough to hold at least a volume of liquid that is between about 380 liters and about 38000 liters.

Wastewater treatment according to present invention has many advantages over the conventional wastewater treatment technology. At a minimum, conventional wastewater treatment processes release noxious byproducts of anaerobic and aerobic digestion into the atmosphere, some of which are believed to contribute to the greenhouse effect. In sharp contrast, the present invention offers novel systems and methods to process these byproducts to generate clean energy and promote production of useful downstream products. In preferred embodiments of the novel systems and methods of the present invention, a portion of the treated wastewater is used to process the byproducts as mentioned above. It is counter to conventional wisdom that treated or purified water obtained from wastewater treatment should be used to treat environmentally harmful byproducts because after putting a substantial amount of energy in treating wastewater, conventional wastewater techniques teach away from wasting that energy by contaminating that treated water. As a result, conventional wastewater treatment processes fail to recognize, among other things, that a portion of the treated water can be used to convert byproducts of wastewater treatment into clean energy. The present invention provides a substantially closed system that treats wastewater and recycles a portion of that treated wastewater to convert noxious byproducts of wastewater treatment into useful energy. By way of example, if the closed system is implemented on a farm, then the wastewater generated at the farm can be treated and at the same time be used to produce clean energy for the farm.

In other respects unrelated to treatment of byproducts, at a minimum, conventional wastewater treatment processes fail to recognize: (i) that decomposition of organic matter depletes soluble oxygen in wastewater constantly during various treatment steps; (ii) the need to substantially maintain the level of dissolved oxygen in wastewater at various stages is important for effective treatment; and (iii) that failure to substantially maintain level of dissolved oxygen and lower solid content through each stage of wastewater treatment causes a reversible reaction which reverses the treatment accomplished in previous treatment steps.

To this end, various steps in preferred embodiments of the present invention recognize the need to drive down BOD, solid content, and nutrient level and maintain or increase level of dissolved oxygen in wastewater. In preferred embodiments of the present invention, wastewater undergoes different types of treatment. By way of example, BOD-creating solids are removed first. Then, the organic matter is consumed by bacteria. Next, nutrients present in wastewater are removed. After performing a first type of treatment, however, the present invention recognizes the need to stabilize the wastewater before advancing it to a second type of treatment. Stabilizing involves preventing a meaningful change in certain important properties of wastewater, e.g., BOD level, dissolved oxygen level, solid content level, and nutrient level, which are susceptible to changing to undesired values by a reversible reaction. Specifically, by lowering BOD levels and solid content and increasing or substantially maintaining dissolved oxygen levels in wastewater throughout the various stages, the present invention effectively transitions from one treatment type to another, without suffering from drawbacks of a reversible reaction.

In accordance with one embodiment, the inventive process using system 100 of FIG. 1A may begin when a treatment system 100 receives wastewater for treatment directly from an anaerobic tank (e.g., anaerobic tank 102 of FIG. 1A). Inside anaerobic tank 102, complex organic material is broken down into smaller constituent organic material by anaerobic bacteria under anaerobic conditions. By way of example, inside anaerobic tank 102, a temperature may be a value that is between about 30° C. and 40° C., a pressure that is about 1 atmosphere, and a volume that is between about 10 gallons per minute and about 15,000 gallons per minute. The volume of the tank is completely scalable and can be higher than 15,000 gallons per minute so long as the necessary amount of equipment is used to process a large amount of liquid in parallel.

In the anaerobic tank, the wastewater is treated with microorganisms that carry out anaerobic digestion, causing the release of biogas 128 that is captured atop an anaerobic tank and delivered to a tank (e.g., tank 126 of FIG. 1B), which is preferably a scrubber and is capable of separating methane from the other components of biogas. The wastewater is then immediately advanced for solid removal as one type of treatment. In a preferred embodiment of the present invention, solid removal is carried out methodically in different steps. It is noteworthy that in this embodiment, not only are solids removed at different steps, but the inventive process is designed to substantially maintain the level of dissolved oxygen in wastewater during these steps to avoid a reversible reaction.

Solid removal preferably begins with removal of relatively large solids from wastewater using a mechanical technique. By way of example, a solids separator such as the one shown in FIG. 1A is preferably used for pressing wastewater containing solids because it also introduces air into the wastewater during the pressing action. As a result, pressing not only removes large solids from wastewater but also maintains the level of dissolved oxygen in wastewater. At this early stage of solid removal, an aerobic process ensures a natural biological degradation and purification process in which bacteria that thrive in oxygen-rich environment break down and digest the organic matter. Maintaining oxygen levels during solid removal ensures that such bacteria do not die off and that level of BOD-contributing solids and solid content in wastewater does not increase. Undesired increase in BOD-contributing solids at this stage would defeat the ultimate purpose of removing the BOD-contributing solids in this step. In other words, during a single treatment step, lowering solid content, lowering BOD level, and substantially maintaining or increasing level of dissolved oxygen in wastewater prevents a reversible reaction that increases BOD, solid content, and/or lowers level of dissolved oxygen in wastewater.

After removing large solids, preferred embodiments of the present invention focus on the removal of medium-sized particles using small air bubbles. In this treatment step, medium-sized solids are carried by an upward motion of air bubbles and removed as explained previously. As a result, bubbles remove BOD-contributing solids, lower solid content, and introduce oxygen simultaneously to substantially maintain or increase a level of dissolved oxygen in wastewater. The advantages of lowering BOD and solid content, and at the same time substantially maintaining or increasing a level of dissolved oxygen in wastewater realized in the previous step, are also realized in this step.

For removal of finer solids from wastewater, the inventive process in a preferred embodiment moves to a tank, such as SRT 108 as shown in FIG. 1A. This tank also stabilizes the wastewater before removal of organic matter commences. Specifically, the tank is designed to remove fine solid particles using a screen when diffused air flow is used inside the tank. Such air flow provides cleaning action to remove the solid build up on the screen and introduces oxygen into wastewater. The advantages of lowering BOD and solid content in wastewater, and at the same time substantially maintaining or increasing level of dissolved oxygen in wastewater realized in the previous steps, are also realized in this step.

Next, the inventive process preferably moves to removal of organic matter as another type of treatment. In this stage of treatment, preferably in a BCR, such as the one shown in FIG. 1A, microorganisms in the presence of biological chips consume organic matter. The microorganisms release gas containing ammonia and sulfur. Various steps of the present invention (described below with reference to FIG. 1C) provide a means to clean this gas with recycled wastewater 125. Consumption of organic matter by microorganisms is enhanced by the presence of a blower which introduces oxygen into wastewater, increasing level of dissolved oxygen in wastewater. With removal of organic matter, wastewater has lower BOD level and solid content and increased level of dissolved oxygen. Microorganisms after consuming a substantial amount of organic material, however, die off and increase both BOD level and solid content. If the dead microorganisms are not timely removed, level of dissolved oxygen in wastewater will drop and a reversible reaction will increase BOD level and solid content in wastewater.

As a result, in the next treatment step, the present invention offers provisions to remove dead microorganisms from wastewater. To this end, preferably, first anaerobic treatment and then an aerobic treatment is used. It is noteworthy that in preferred embodiments of the present invention, wastewater at this stage is subjected to anaerobic digestion for a second time. In the anaerobic treatment at this stage, preferably an SRT is sealed off to make sure that all aerobic microorganisms die off. At the same time, using screens inside the SRT, dead microorganisms are removed using screens inside the SRT. This lowers both BOD level and solid content in wastewater. But, before wastewater can advance to the next stage, the present invention realizes that level of dissolved oxygen in wastewater should increase.

In the next step, aerobic treatment is preferably carried out using a DAF tank such as the one shown in FIG. 1A. Diffused air flow inside the DAF tank raises level of dissolved oxygen and removes residual solids. Now, wastewater having lower BOD level and solid content and higher level of dissolved oxygen is ready for the next stage of treatment.

In the next stage, wastewater is treated in algal pond, preferably an HRAP such as the one shown in FIG. 1A, to effectively remove nutrients from wastewater. Nutrient removal from wastewater is carried out by algae, which in the presence of an operating radiation source effectively consumes nutrients. Algae also boost level of dissolved oxygen in wastewater. However, level of dissolved oxygen in wastewater may not be high enough to meet the requirement of discharge to environment.

It is important to recognize that if after anaerobic treatment aerobic treatment did not follow, then wastewater with high concentration of ammonia, as opposed to nitrates or nitrogen, would have entered the HRAP posing a risk of killing algae. Thus, anaerobic treatment followed by aerobic treatment ensures that wastewater is prepared for nutrient removal in the subsequent steps.

In the next treatment steps, dissolved oxygen level in wastewater is raised to allow discharge to environment. Preferably a DAF tank is used to provide diffused air flow for raising level of dissolved oxygen and removing algae and other solids from wastewater. Solid removal lowers BOD level and solid content in wastewater. Then, for removal of finer particles, wastewater is advanced to an SRT which uses diffused air for removal of solids from and introduction of oxygen to wastewater. Consequently, wastewater has the requisite high level of dissolved oxygen, lower BOD level, and solid content for discharge into environment.

Although wastewater is now ready for discharge into environment, preferred embodiments treat this wastewater in a maturation pond where it is exposed to elements found in the environment. Wastewater matures and is adapted to the natural environment in the maturation pond, from where it is discharged to the environment.

As shown in FIG. 1A, solids removal is carried out at least partially in DAF tank 106 and SRT 108. During such solids removal, however, aerobic bacteria are typically present. As a result, when oxygen is added to these tanks during solids removal, these tanks are not only efficiently removing solids, but are effectively carrying out aerobic digestion on the wastewater well before that wastewater reaches the BCR reactors, where the wastewater further undergoes aerobic digestion.

In accordance with preferred embodiments, the inventive processes on a parallel track treat the gaseous byproducts produced during wastewater treatment. By way of example, biogas (e.g., methane, carbon dioxide, ammonia, hydrogen, and sulfur) resulting from anaerobic digestion is delivered from an anaerobic tank to another tank, which is preferably a scrubber. Before biogas is conveyed to the tank, the tank is filled with water, which is preferably treated water obtained after the conclusion of a wastewater treatment process. Inside the tank, water contacts the biogas. In preferred embodiments of the present invention, biogas is in the form of tiny micro bubbles when it contacts water. Biogas in bubble form provides a high surface area between the biogas/water interface to allow certain gases in the biogas mixture to dissolve in water. However, as methane does not dissolve in water, it exhausts from the tank. Instead of releasing methane exhaust into the atmosphere, as conventional processes do, the present invention delivers methane for further processing to an electrical generator located downstream. From inside the tank, a stream of water, which contains certain biogas components dissolved therein, is discharged to a tank for solids removal (e.g., DAF tank 106 of FIG. 1A).

The methane exhaust is further processed (e.g., in system 170 of FIG. 5) to produce electricity and other useful products. Specifically, methane gas is delivered to an electrical generator, which converts methane to electricity and produces other byproduct gases (e.g., at least one of $CO_2$, $SO_X$, and $NO_X$). These gaseous byproducts are next conveyed to a tank, preferably a scrubber, where they are treated substantially similarly to the treatment of biogas as a byproduct (i.e., tiny micro bubbles of the gaseous mixture are conveyed through water to dissolve those components of the gaseous mixture which dissolve in water). Preferably, treated water is used to process the byproduct gas. Residual gas not dissolved in water is recirculated back to the tank for further processing—i.e., multiple passes may be made through the tank to dissolve the residual gases in water. Water effluent that includes the dissolved gases is conveyed to an algal pond (e.g., HRAP 118 of FIG. 1A) to promote algae growth. With regard to the energy produced by the electrical generator, the amount of energy is significant. By way of example, for a farm that raises dairy cattle, an electrical generator produces between about 1 and about 5 kilowatts of electricity per day per animal.

Processing of wastewater by aerobic digestion also produces byproducts, which are treated according to the preferred embodiments of novel systems and methods of the present invention. In accordance with one preferred embodiment, the inventive processes may begin when byproduct gas is received into a tank, preferably a scrubber, after wastewater has undergone aerobic digestion (e.g., in BCRs 110 and 112). Byproduct gas (e.g., shown denoted by reference numeral 142 of FIG. 1C) of aerobic digestion includes at least one of ammonia gas and sulfur gas. Before the byproduct gas is received, however, the tank is filled with water, which is preferably treated wastewater. In preferred embodiments, byproduct gas processed according to the present invention is introduced in bubble form. A certain amount that is soluble of certain components of the byproduct gas dissolve in water and the remaining, undissolved amounts or components, such as residual ammonia gas or residual sulfur gas, are recycled back to the tank further processing (i.e., for further attempts to dissolve the residual ammonia gas and sulfur gas in water in subsequent contact cycles in the tank). The resulting effluent stream enriched with the soluble byproduct gas components is discharged from the tank and processed depending on the concentration of aqueous ammonia and sulfur in the water stream.

Using an ammonia concentration sensor, the concentration of ammonia in the wastewater is determined. If the effluent contains ammonia in a concentration that is greater or equal to a predetermined concentration value, then the ammonia is typically sent back to the BCR reactor, from where the byproduct gas had originated. In this BCR, the residual ammonia gas undergoes further processing so that it is reduced to simpler molecular forms, such as nitrates, nitrites, or nitrogen, which are useful for algae growth (e.g., in HRAP 118 of FIG. 1A). If, however, the concentration of ammonia is sufficiently low, i.e., below the predetermined concentration value, then the effluent stream is considered to have simpler forms of nitrogen which are useful for algae growth. Accordingly, effluent streams with such low concentrations of ammonia are advanced to an algal pond (e.g., in HRAP 118 of FIG. 1A).

In other preferred embodiments of the present invention, the concentration of sulfur is similarly discerned. If the sulfur concentration sensor detects the concentration of sulfur gas to be greater than or equal to a predetermined concentration value, then the effluent stream is returned back to the BCR reactor, from where the byproduct gas had originated. In this BCR, the residual sulfur gas undergoes further processing so that it is consumed if not in the first pass back to the BCR, then in the subsequent ones. Alternatively, if the sulfur concentration detects the concentration of sulfur gas to be less than the predetermined concentration value, then the effluent stream advances to the algal pond. In light of the above disclosure, those skilled in the art will recognize that in preferred embodiments of the present invention, the effluent stream of the tank (e.g., a scrubber) are only advanced to an algal pond when both concentration of aqueous ammonia and sulfur gas are below their respective predetermined concentration values. However, compared to ammonia, sulfur is known to dissipate relatively quickly and, therefore, in preferred embodiments of the present invention, only the concentration of ammonia in the effluent stream is monitored as described above.

Although illustrative embodiments of this invention have been shown and described, other modifications, changes, and substitutions are intended. Accordingly, it is appropriate that the appended claims be construed broadly and in a manner consistent with the scope of the disclosure, as set forth in the following claims.

What is claimed is:

1. A method for removing a gas, said method comprising:
receiving into a first tank a gaseous mixture including ammonia gas;
receiving water into said first tank;
contacting said gaseous mixture including ammonia gas with said water inside said first tank to produce an effluent stream of water having dissolved therein aqueous ammonia and produce a residual gaseous mixture including residual ammonia gas;
dispensing from said first tank said residual gaseous mixture including residual ammonia gas;
detecting concentration of aqueous ammonia by volume in said effluent stream; and
conveying said effluent stream including water which has dissolved therein aqueous ammonia to a second tank which breaks down aqueous ammonia if amount of aqueous ammonia in said effluent water stream is greater than or equal to a predetermined ammonia value, or conveying said effluent stream to an algal pond if amount of ammonia in said effluent stream is less than said predetermined ammonia value.

2. The method of claim 1, wherein said dispensing includes recirculating said residual gaseous mixture from outlet of said first tank to an inlet of said first tank.

3. The method of claim 2, wherein a content of organic matter in said wastewater after aerobic digestion is between about 0% by volume and about 4% by volume.

4. The method of claim 1, wherein in said second tank, aerobic digestion of said effluent stream is performed to produce said gaseous mixture including ammonia gas.

5. The method of claim 4, wherein aerobic digestion is carried out in a biological chip reactor.

6. The method of claim 1, wherein said water is purified water.

7. The method of claim 6, wherein said purified water is water obtained from a wastewater treatment facility.

8. The method of claim 1, wherein said contacting includes passing bubbles of said gaseous mixture through said water.

9. The method of claim 1, wherein said predetermined ammonia value is between about 0 ppm and about 10 ppm.

10. The method of claim 9, wherein said algal pond is a high-rate algal pond.

11. The method of claim 1, wherein said conveying said effluent stream includes breaking down in said second tank nitrogen composition of said aqueous ammonia into less complex form.

12. The method of claim 1, wherein said receiving said water into said first tank includes receiving water from a maturation pond.

13. The method of claim 1, wherein said conveying said effluent stream includes using an ammonia concentration sensor to measure said amount of aqueous ammonia in said effluent water stream.

14. The method of claim 13, wherein said ammonia concentration sensor is coupled to two valves such that if said ammonia concentration sensor measures amount of aqueous ammonia in said effluent water stream to be greater than or equal to said predetermined ammonia value, a first valve conveys said effluent stream including water which has dissolved therein aqueous ammonia from said first tank to said second tank, and if said ammonia concentration sensor measures amount of aqueous ammonia in said effluent water stream to be less than said predetermined ammonia value, said second valve conveys said effluent stream from said first tank to said algal pond.

15. The method of claim 1, wherein said receiving into said first tank said gaseous mixture includes receiving said gaseous mixture that is produced in a biological chip reactor.

16. The method of claim 1, wherein said receiving into said first tank said gaseous mixture includes receiving said gaseous mixture resulting from aerobic digestion.

17. A method for removing a byproduct gas after aerobic digestion, comprising:
  receiving into a first tank a gaseous mixture including sulfur gas;
  receiving water into said first tank;
  contacting said gaseous mixture including sulfur gas with said water inside said first tank to produce an effluent stream of water having dissolved therein sulfur and produce a residual gaseous mixture including residual sulfur gas;
  dispensing from said first tank said residual gaseous mixture including residual sulfur gas;
  detecting concentration of dissolved sulfur by volume in said effluent stream; and
  conveying said effluent stream including water which has dissolved therein sulfur to a second tank which breaks down sulfur, if amount of sulfur in said effluent water stream is greater than or equal to a predetermined sulfur value, or conveying said effluent stream to an algal pond if amount of sulfur in said effluent stream is less than said predetermined sulfur value.

18. The method of claim 17, wherein in said second tank, aerobic digestion of said effluent stream is performed to produce said gaseous mixture including sulfur gas.

19. The method of claim 17, wherein said contacting includes passing bubbles of said gaseous mixture through said water.

20. The method of claim 17, wherein said receiving said water into said first tank includes receiving water from a maturation pond.

21. The method of claim 17, wherein said conveying said effluent stream includes using a sulfur concentration sensor to measure said amount of sulfur in said effluent water stream.

22. The method of claim 21, wherein said sulfur concentration sensor is coupled to two valves such that if said sulfur concentration sensor measures amount of sulfur in said effluent water stream to be greater than or equal to said predetermined sulfur value, a first valve conveys said effluent stream including water which has dissolved therein sulfur from said first tank to said second tank, and if said sulfur concentration sensor measures amount of sulfur in said effluent water stream to be less than said predetermined sulfur value, said second valve conveys said effluent stream from said first tank to said algal pond.

23. The method of claim 17, wherein said receiving into said first tank said gaseous mixture includes receiving said gaseous mixture that is produced in a biological chip reactor.

24. The method of claim 17, wherein said receiving into said first tank said gaseous mixture includes receiving said gaseous mixture resulting from aerobic digestion.

25. A method for removing one or more gases from water, comprising:
  receiving into a first tank a gaseous mixture including at least one of ammonia gas and sulfur gas;
  receiving water into said first tank;
  contacting said gaseous mixture including at least one of said ammonia gas and said sulfur gas with said water inside said first tank to produce an effluent stream of water having dissolved therein said at least one of aqueous ammonia and sulfur and produce a residual gaseous mixture including at least one of residual ammonia gas and residual sulfur gas; and
  dispensing from said first tank said residual gaseous mixture including at least one of residual ammonia gas and residual sulfur gas;
  detecting concentration of aqueous ammonia by volume in said effluent stream; and
  discharging said effluent stream including water which has dissolved therein said at least one of aqueous ammonia and sulfur; and
  conveying said effluent stream including water which has dissolved therein at least one of aqueous ammonia and sulfur to a second tank which breaks down aqueous ammonia or consumes sulfur gas, if amount of aqueous ammonia in said effluent water stream is greater than or equal to a predetermined ammonia value, or conveying said effluent stream to an algal pond if amount of ammonia in said effluent stream is less than said predetermined ammonia value.

* * * * *